(12) United States Patent
Muehlsteff (10) Patent No.: US 9,936,920 B2
(45) Date of Patent: Apr. 10, 2018

(54) DEVICE AND METHOD TO IMPROVE DEPENDABILITY OF PHYSIOLOGICAL PARAMETER MEASUREMENTS

(71) Applicant: KONINKLIJKE PHILIPS N.V., Eindhoven (NL)

(72) Inventor: Jens Muehlsteff, Aachen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 5 days.

(21) Appl. No.: 14/426,166

(22) PCT Filed: Sep. 3, 2013

(86) PCT No.: PCT/IB2013/058251
§ 371 (c)(1),
(2) Date: Mar. 5, 2015

(87) PCT Pub. No.: WO2014/037874
PCT Pub. Date: Mar. 13, 2014

(65) Prior Publication Data
US 2015/0250426 A1    Sep. 10, 2015

Related U.S. Application Data

(60) Provisional application No. 61/698,751, filed on Sep. 10, 2012.

(51) Int. Cl.
*A61B 5/00* (2006.01)
*A61B 5/0205* (2006.01)
(Continued)

(52) U.S. Cl.
CPC .......... *A61B 5/7221* (2013.01); *A61B 5/0059* (2013.01); *A61B 5/0205* (2013.01);
(Continued)

(58) Field of Classification Search
CPC . A61B 5/0059; A61B 5/0205; A61B 5/02055; A61B 5/0402; A61B 5/113;
(Continued)

(56) References Cited

U.S. PATENT DOCUMENTS

| 4,860,759 A | 8/1989 | Kahn et al. |
| 5,876,350 A * | 3/1999 | Lo ...................... A61B 5/02438 |
| | | 600/502 |

(Continued)

FOREIGN PATENT DOCUMENTS

| JP | 2012157435 | 8/2012 |
| WO | 2004032715 A2 | 4/2004 |
| WO | 2011082341 A1 | 7/2011 |

OTHER PUBLICATIONS

Aubert, X. L., et al.; Non-invasive Cuff-less Measurements of the Arterial Blood Pressure: What does Pulse-Transit-Time tell us all about?; 2006; IEEE Proc. ESGCO; pp. 211-214.
(Continued)

*Primary Examiner* — Christopher A Flory (57) ABSTRACT

Self measurements of physiological parameters such as blood pressure are prone to errors and artifacts since they are often not done according to established and standardized protocols i.e., such that predetermined conditions for a reliable measurement are not met. To determine whether the predetermined conditions for a reliable measurement are met one or more physiological and environmental sensors are used to determine a measurement context. The obtained sensor data is compared with predetermined thresholds to determine whether the context allows a reliable self test. In case the predetermined conditions are not met based on the obtained sensor data instructions are given to guide the subject that wants to do a self test.

20 Claims, 5 Drawing Sheets

(51) Int. Cl.
*A61B 5/1495* (2006.01)
*A61B 5/0402* (2006.01)
*A61B 5/113* (2006.01)
*A61B 7/02* (2006.01)
*G06F 19/00* (2018.01)
*A61B 5/022* (2006.01)
*A61B 5/053* (2006.01)

(52) U.S. Cl.
CPC ........ *A61B 5/02055* (2013.01); *A61B 5/0402* (2013.01); *A61B 5/113* (2013.01); *A61B 5/1495* (2013.01); *A61B 5/6804* (2013.01); *A61B 7/02* (2013.01); *A61B 5/022* (2013.01); *A61B 5/0531* (2013.01); *A61B 5/7203* (2013.01); *A61B 2560/0242* (2013.01); *G06F 19/3406* (2013.01)

(58) Field of Classification Search
CPC ... A61B 5/1495; A61B 5/6804; A61B 5/7221; A61B 7/02
USPC .................................................. 600/300, 301
See application file for complete search history.

(56) References Cited

U.S. PATENT DOCUMENTS

| | | | |
|---|---|---|---|
| 2004/0133081 A1* | 7/2004 | Teller | A61B 5/01 600/300 |
| 2004/0152957 A1* | 8/2004 | Stivoric | A61B 5/01 600/300 |
| 2005/0080461 A1* | 4/2005 | Stahmann | A61B 5/0031 607/17 |
| 2005/0115561 A1* | 6/2005 | Stahmann | A61B 5/0031 128/200.24 |
| 2006/0031102 A1* | 2/2006 | Teller | A61B 5/411 705/3 |
| 2006/0224051 A1* | 10/2006 | Teller | A61B 5/02055 600/300 |
| 2006/0264730 A1* | 11/2006 | Stivoric | A61B 5/0205 600/390 |
| 2008/0082001 A1* | 4/2008 | Hatlestad | A61B 5/02405 600/481 |
| 2008/0146958 A1* | 6/2008 | Guillory | A61B 5/0476 600/544 |
| 2008/0161654 A1* | 7/2008 | Teller | A61B 5/01 600/300 |
| 2008/0214941 A1* | 9/2008 | Lin | A61B 5/02405 600/485 |
| 2008/0214942 A1* | 9/2008 | Oh | A61B 5/02125 600/485 |
| 2008/0228089 A1* | 9/2008 | Cho | A61B 5/02125 600/485 |
| 2009/0018453 A1 | 1/2009 | Banet et al. | |
| 2009/0177225 A1 | 7/2009 | Nunez et al. | |
| 2009/0275805 A1 | 11/2009 | Lane et al. | |
| 2010/0145730 A1* | 6/2010 | Abreu | G06K 7/10861 705/3 |
| 2010/0223581 A1* | 9/2010 | Manolescu | G06Q 10/00 715/853 |
| 2010/0249551 A1 | 9/2010 | Miller | |
| 2010/0286532 A1* | 11/2010 | Farringdon | A61B 5/0428 600/483 |
| 2010/0332173 A1 | 12/2010 | Watson et al. | |
| 2011/0055717 A1* | 3/2011 | Firminger | G06Q 10/10 715/747 |
| 2011/0061647 A1* | 3/2011 | Stahmann | A61B 5/0031 128/202.16 |
| 2011/0152632 A1* | 6/2011 | Le Neel | A61B 5/0022 600/300 |
| 2011/0224500 A1 | 9/2011 | Banet et al. | |
| 2011/0288422 A1 | 11/2011 | Chen et al. | |
| 2012/0245439 A1* | 9/2012 | Andre | A61B 5/0205 600/310 |
| 2012/0296225 A1* | 11/2012 | Zhang | A61B 5/7264 600/508 |
| 2013/0053653 A1* | 2/2013 | Cuddihy | A61B 5/0205 600/301 |
| 2013/0096441 A1* | 4/2013 | Osorio | A61B 5/0245 600/484 |
| 2013/0144919 A1* | 6/2013 | Firminger | G06F 17/30091 707/803 |
| 2013/0171599 A1* | 7/2013 | Bleich | A61B 5/0456 434/247 |
| 2013/0274830 A1* | 10/2013 | Skelton | A61N 1/3605 607/62 |
| 2013/0317837 A1* | 11/2013 | Ballantyne | A61M 1/1037 705/2 |
| 2014/0128690 A1* | 5/2014 | LeBoeuf | A61B 5/4857 600/301 |
| 2014/0188516 A1* | 7/2014 | Kamen | G06F 19/3406 705/3 |
| 2015/0143601 A1* | 5/2015 | Longinotti-Buitoni | A61B 5/0002 2/69 |
| 2015/0154364 A1* | 6/2015 | Biasi | G06F 19/3412 709/223 |

OTHER PUBLICATIONS

Morren, G., et al.; Fall prediction based on vital sign monitoring; 2008; Philips Technical Report PR-TN 2008/00411; pp. 1-53.
Muehlsteff, J., et al.; Cardiac Status Assessment with a Multi-Signal Device for Improved Home-based Congestive Heart Failure Management; 2011; IEEE Proc. EMBS; pp. 876-879.
Muehlsteff, J., et al.; Continuous Cuff-less Blood Pressure Monitoring based on the Pulse Arrival Time Approach: The Impact of Posture; 2008; IEEE Proc. EMBC; pp. 1691-1694.
Muehlsteff, J., et al.; Cuffless Estimation of Systolic Blood Pressure for Short Effort Bicycle Tests: The Prominent Role of the Pre-Ejection Period; 2006; IEEE Proc. EMBS; pp. 5088-5092.
Wagner, S., et al.; Challenges in Blood Pressure Self-Measurement; 2012; International Journal of Telemedicine and Applications; pp. 1-8.

* cited by examiner

Fig. 5

DEVICE AND METHOD TO IMPROVE DEPENDABILITY OF PHYSIOLOGICAL PARAMETER MEASUREMENTS

CROSS REFERENCE TO RELATED APPLICATIONS

This application is a national filing of PCT application Serial No. PCT/IB2013/058251, filed Sep. 3, 2013, published as WO 2014/037874 A1 on Mar. 13, 2014, which claims the benefit of U.S. provisional application Ser. No. 61/698,751 filed Sep. 10, 2012, which is incorporated herein by reference.

FIELD OF THE INVENTION

The invention is related to the field of measurement of physiological parameters, in particular to the unassisted measurement of physiological parameters of a subject.

BACKGROUND OF THE INVENTION

One of the vital signs of a person often measured is the blood pressure (BP). Though the basic procedure of measuring physiological parameters such as blood pressure may be a simple one, there are certain conditions to be met and protocols to be adhered to, just before and during the measurement to obtain dependable measurement values.

Changes in demography, ageing populations for instance, the increasing healthcare costs, expected shortage of medical staff, growing demand for improved healthcare in emerging and developing countries will drive further changes in the healthcare systems. Patients will not only be monitored sporadically in the hospitals during acute phases but also in low acuity settings and even at home, where they are often unsupervised or unassisted by trained staff. To enable this, the patients may even be asked to make reliable measurements themselves (i.e. monitoring everywhere, ubiquitous monitoring).

The published patent application US20110224500 describes a body-worn vital sign monitor that measures a patient's vital signs (e.g. blood pressure, SpO2, heart rate, respiratory rate, and temperature) while simultaneously characterising their activity state (e.g. resting, walking, convulsing, falling) and posture (upright, supine). The monitor processes this information to minimize corruption of the vital signs and associated alarms/alerts by motion-related artifacts.

In this case, the measurements are made at whatever conditions prevail at the time of the measurements and using other physiological parameters the vital sign values are processed to reduce the artifacts.

However, there are many patients either at home or in a care facility who need not be monitored on a continuous basis but whose physiological parameters need to be measured accurately, adhering to measurement protocols, to obtain dependable readings of the physiological parameters, a few times a day. This is increasingly being done by the patient himself/herself. (In the text here after, the masculine pronoun will be used for clarity though both masculine and feminine are implicitly intended) In such cases, however, it has to be ensured that the patient measures his own physiological parameters under proper and well-defined conditions that would make the measured physiological parameters values dependable for decisions based on them. Further, when physiological parameters values are stored for recognizing a trend in the physiological parameters, if the measured values are not dependable, as an obvious consequence, the trend also is rendered undependable.

Physiological parameters measurements done by the patient himself are prone to errors and artifacts since they are often not done according to established and standardized protocols. For example, a patient is expected to have rested for at least five minutes immediately before the start of a Blood Pressure (BP) measurement; he should not talk during the measurement; the measurements must be made when the body is in a prescribed position Ankle brachial pressure index and Pulse wave velocity are other examples of such measurements that require predefined conditions for dependable measurements. Since many patients do not comply with such requirements consistently, physiological parameter measurements are often difficult to interpret for the clinicians/physicians and are of limited value in disease management systems for decision support.

However, new monitoring and treatment concepts in unsupervised scenarios e.g. in home monitoring/tele-monitoring need accurate physiological parameter measurements as key input parameters. One example is the management of congestive heart failure patients as described in the paper "Cardiac Status Assessment with a Multi-Signal Device for Improved Home-based Congestive Heart Failure Management", by Jens Muehlsteff et al, called "Hemodynamic Tailoring" aiming at personalized treatment and therapy using hemodynamic variables to assess the patient's health status. In general any decision support system requires reliable measurements. This concept inherently provides means to check the quality of a physiological parameter measurement. If the quality of a measurement is considered too low, the system may reject a BP measurement supplied to it as input.

SUMMARY OF THE INVENTION

Thus there is a need for a device and a method that promotes dependable physiological parameter measurements. This need is addressed with a device for determining if predetermined conditions for a first physiological parameter measurement of a subject are met as defined in claim 1. The device according to claim 1 enables the measurement of a physiological parameter of a subject when one or more predefined conditions are met. The measurement may be made by the subject or triggered by the subject or measured automatically when the predefined or preferred conditions are met.

The device according to claim 1 is arranged to measure one or more physiological and one or more environmental parameters. The values of these parameters are used to infer the subject's status. Here, status means whether the physiological and environmental parameters are in steady state or not and whether they meet pre-defined measurement protocols or not. There may be additional requirements too. For instance that the patient has been at rest and in the predefined posture for a predetermined length of time before and during the measurement of the first physiological parameter or that the subject has not spoken for a certain period of time or during the time period used for measurement of the first physiological parameter.

In the further text the term 'context' is used. The context encompasses the values of the physiological parameters, the values of the environmental parameters wherein the environmental parameters include, for example, the subject's position, how long the subject has been in the prescribed position, whether the subject has been talking and so on. When all the predetermined conditions are met, the context is said to be suitable or appropriate for the first physiological parameter measurement to be made.

In a preferred embodiment the one or more sensors are disposed in a wearable electronic garment (here after it may be referred to as garment) such that, when worn in a predefined way, the sensors are disposed on the subject's body in positions appropriate for measuring various physiological parameters or vital signs of the subject. In another embodiment, the device is configured to guide the subject by conveying predefined instructions to take specific actions to make the context appropriate for the measurement. In another embodiment, the decision unit automatically triggers the physiological parameter measurement when the context is appropriate.

Further the need is also address with a method of determining if predetermined conditions for a physiological parameter measurement of a subject are met, according to claim 10.

According to the disclosed method values of various physiological and environmental parameters are measured. When the values of the parameters meet certain predefined requirements and the context meets predetermined conditions, it indicates that a dependable physiological parameter measurement may be made. This is either indicated so that the first physiological parameter measurements are made or the acquisition of first physiological parameter measurement signals, from a cuff-based sensor for BP measurement, for instance, is enabled. The signals acquired are then processed to get the BP of the subject.

Cuff based measurement may be made with a sphygmomanometer cuff having an electronic pressure sensor to sense cuff pressure oscillations. In an embodiment the sphygmomanometer cuff further comprises signal processing means to interpret the transducer signals and calculate the BP values. The sphygmomanometer cuff may also have means for automatic inflation and deflation of the cuff.

The cuff may be inflated initially to a pressure in excess of the systolic arterial pressure and then reduced to below diastolic pressure over a period of about 30 seconds. When blood flow is present, but restricted, the cuff pressure, which is monitored by the pressure sensor, will vary periodically in synchrony with the cyclic expansion and contraction of the brachial artery. In other words, it oscillates. The values of systolic and diastolic pressures are computed, from the raw data using a suitable algorithm. In an embodiment of the device according to claim 7 a sphygmomanometer cuff is used as a BP sensor. The determined blood pressure may be displayed on the device for a care giver or conveyed to any other device at a remote location for interpretation.

It is to be understood that if the values of the parameters change during the acquisition of the signals and one or more of them are no longer within the predetermined limits, in other words, the context changes such that predetermined conditions are no longer met, the measurement is discontinued or disabled. The subject speaking during the acquisition is an event, for example, that makes the context inappropriate for the first physiological parameter measurement. Then, that state is indicated so that the first physiological parameter measurement is abandoned or acquisition of first physiological parameter measurement signals is disabled.

BRIEF DESCRIPTION OF THE DRAWINGS

These and other aspects of the disclosed device and method are described in detail with reference to the following figures, wherein:

FIG. 3, comprising

DETAILED DESCRIPTION OF EMBODIMENTS

Figure 1:
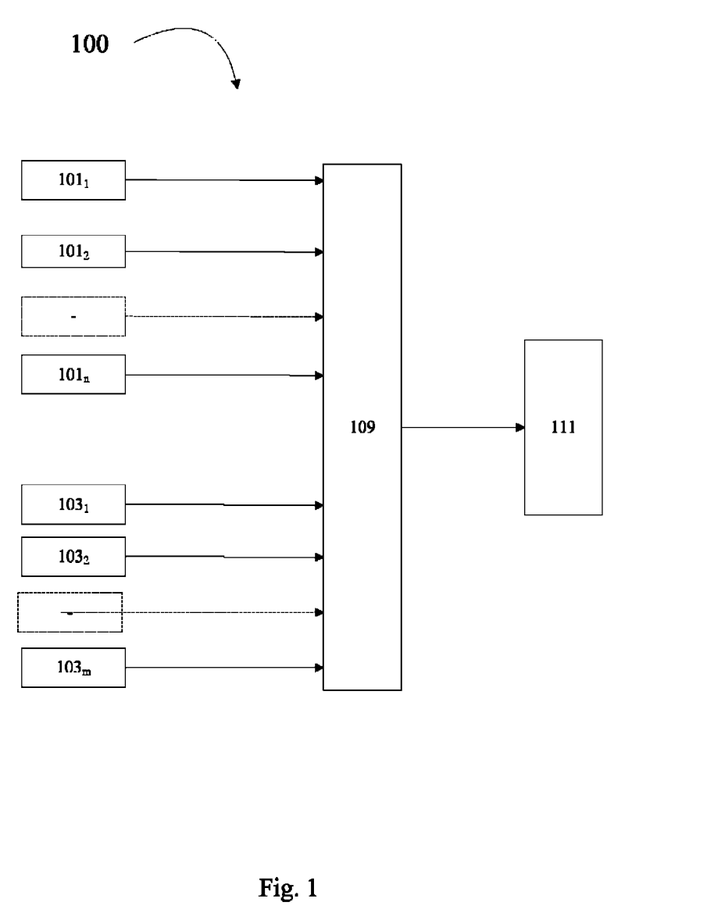
FIG. 1 is a schematic diagram of the disclosed device.

FIG. 1 shows the schematic block diagram of an embodiment of the disclosed device. In the description that follows, the term first physiological parameter is used for the physiological parameter that may be measured by the unassisted subject himself or by a caregiver. The other physiological parameters measured to ensure the dependability of the measurement of the first physiological parameter are referred to as the second physiological parameters. The physiological parameter sensors $101_1$, $101_2$ ... $101_n$ are applied to the subject's body surface appropriately. The environmental parameter sensors $103_1$, $103_2$ ... $103_m$ are disposed in the immediate environment of the subject. The one or more physiological sensors $101_1$, $101_2$ ... $101_n$ enable measuring one or more second physiological parameters of the subject and one or more environmental sensors $103_1$, $103_2$ ... $103_m$ enable measuring one or more environmental parameters from the environment of the subject. For instance the physiological sensors for measuring the second physiological parameters may include a heart sound sensor for measuring a pulse rate (beats per minute) and accelerometers for deriving a posture of the subject and/or an activity level of the subject. These are but a couple of examples and it is to be understood that signals from all the sensors are received and the values of the corresponding physiological parameters are measured. Similarly the at least one environmental sensor enables the measuring of environmental parameters. For instance, the environmental sensor may be a microphone for determining if the subject has been speaking. This sensor may also be used to monitor how long the subject has been silent. The air temperature surrounding the subject is sensed and the atmospheric temperature is measured with a temperature sensor. The decision unit 109 decides based on the values of the second physiological parameters such as, for example, pulse rate and posture and the values of environmental parameters such as, for example sound, whether predetermined conditions are met and the first physiological parameter measurement can be made. The output unit 111 outputs the decision in an appropriate fashion. In the simplest case, the output may be a green lamp, for example, indicating that a first physiological parameter measurement may be made.

Once the output unit 111 outputs the decision that a physiological parameter measurement can (or could) be made, a caregiver may measure the physiological parameter in a known way. In certain embodiments the subject himself may trigger a physiological parameter measurement by an automated physiological parameter measuring device based on the output. In one embodiment, the output of the output unit 111 is received by a sphygmomanometer cuff worn by the subject and a cuff based BP measurement is made in response to the received output.

Certain external devices, for instance clinical decision support (CDS) devices use first physiological parameter values as one of the inputs for their operation. In one embodiment, the output unit may convey the measured first physiological parameter values to such a device in a wired or wireless manner. Some such devices also require the context of the measurement of the first physiological parameter. In one embodiment, the output unit may also convey the values of all the physiological and environmental parameters and other data at the time of the first physiological parameter measurement.

However, it is to be noted that the context, once determined as appropriate is dynamic and not static. That means it may change even during the short time required to measure the first physiological parameter manually or acquire the measurement signals of the first physiological parameter. Thus in an embodiment, the device according to the invention continuously measures the physiological parameters and environmental parameters to monitor the context and to determine if predetermined conditions are met. If the context changes during the measurement the decision unit 109 may determine that the predetermined conditions are no longer met and the first physiological parameter measurement may not be made, which is output by the output unit 111. A red lamp, for instance, may be used for indicating that the context is not appropriate for the first physiological parameter measurement. The manual measurement of the first physiological parameter must be abandoned at that time. In the embodiment wherein the measurement of the first physiological parameter is automatic, the acquisition of the signals for a first physiological parameter measurement is stopped and the signals acquired till then are discarded. The device then awaits the context to become suitable again for a first physiological parameter measurement.

The different parameters taken into account and the appropriate sensors are now described. The parameters are neither exhaustive nor any one of them is essential to practice the disclosed device and method. Some of the second physiological parameters measured may be as follows. Heart sound sensors may be applied to the torso of the subject to measure the heart rate or the pulse rate. Electrocardiogram electrodes may be applied to the subject at appropriate places to sense electrical signals of the heart. Apart from the well known data that may be derived from the ECG signals the signals may also be processed to provide the pulse rate Skin temperature measurements may be carried out using the suitable known sensors. Electrical resistance of the skin provides a measure of the relaxed state of the subject and even a sense of the time elapsed since previous exertion. Thoracic impedance sensors provide signals for measuring the breathing rate of the subject. Infrared Photoplethysmograph and near-infrared Photoplethysmograph sensors provide information on SpO2 and also the pulse rate. Combining the ECG information and the plethysmography signals it is possible to estimate the BP also of the subject in an indirect manner. Respiratory Inductance Plethysmography sensors may be used to sense the respiratory rate. Three-axis accelerometers are used to measure the subject's position and posture apart from activity or absence of it.

Similarly, some of the environmental parameters measured may be as follows. Air temperature may be measured with a suitable sensor. Similarly, atmospheric pressure and humidity sensors may be used for measuring atmospheric pressure and relative humidity. Microphones may be used for sensing the environmental noise and also the voice of the subject. A single microphone may be used to sense both or separate microphones may be used for each.

The context derived from the values of the parameters will now be described exemplarily. Predetermined thresholds may be set for one or more second physiological and/or environmental parameter. When the value of the parameter is below or above the thresholds applicable to that parameter, the corresponding parameter may be treated as conducive to the measurement of the first physiological parameter. The physiological and/or environmental parameters for which predetermined thresholds have been set together form the predetermined conditions for the first physiological parameter measurement. Thus when all the second physiological and/or environmental parameters meet predefined criteria (i.e. larger or smaller than predetermined thresholds or between upper and lower thresholds), the context may be declared as appropriate for the measurement of the first physiological parameter.

However, such a decision (that the context is appropriate) may suffer from the fact that factors such as the subject's sex, age, level of fitness and recent medical history may determine the threshold values for each of the parameters. Such being the case, in a further embodiment the rate of change of a second physiological parameter over a predetermined time period is measured and when the rate of change falls below a certain threshold, that parameter may be deemed to meet the predetermined criterion. For example the pulse rate at rest differs from person to person. Thus, instead of measuring the pulse rate of a person the rate of fall of the pulse rate once the person assumes the position for the measurement of the first physiological parameter may be measured and when it falls below a certain rate, the pulse rate parameter may be deemed to be appropriate for the measurement of the first physiological parameter. In a further embodiment a user interface is provided for the device that will allow the values of the different parameters suitable for an individual subject are entered and stored in the device.

Figure 2:
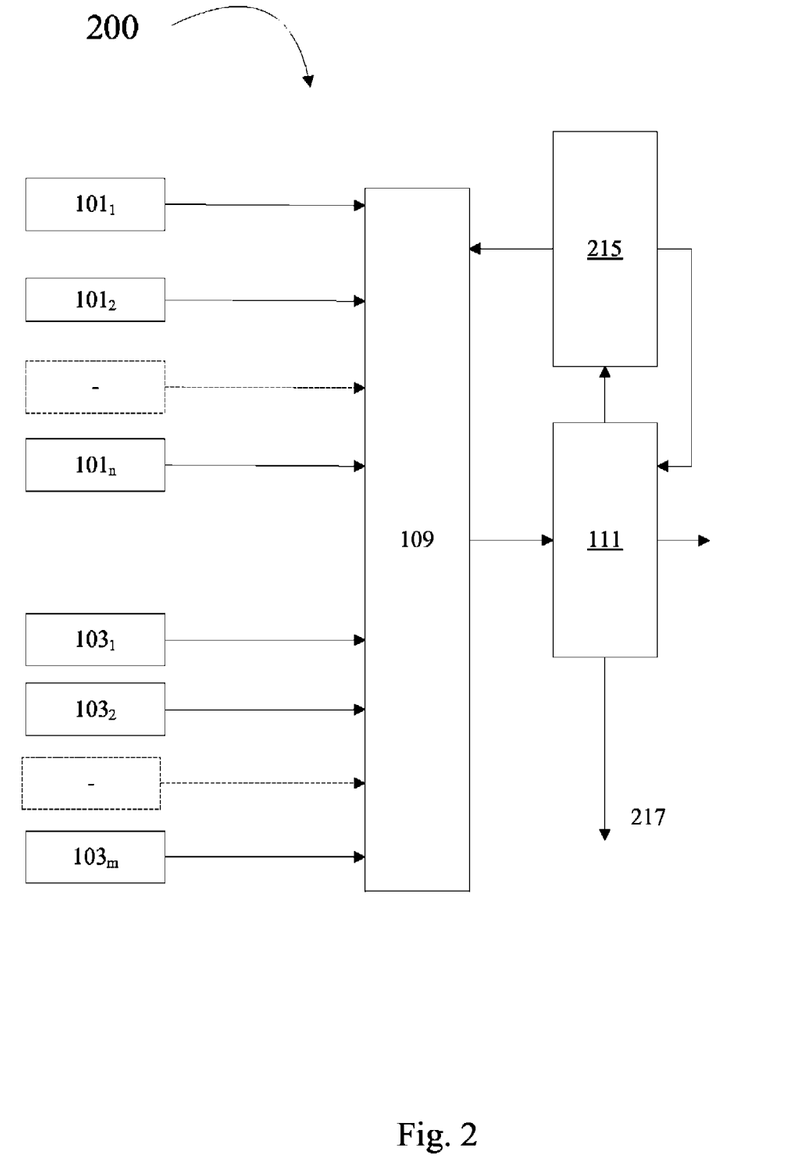
FIG. 2 is a schematic diagram of an embodiment of the disclosed device.

In a preferred embodiment the device is arranged for determining if predetermined conditions for a blood pressure measurement of a subject are met, shown FIG. 2, the device comprises or is operatively connected to a sphygmomanometer cuff 215 for obtaining cuff-based BP measurement signals. The output of the decision unit 109 enables the device to sense the signals from the sphygmomanometer cuff and to calculate the BP, when the context is again appropriate.

Figure 3A:
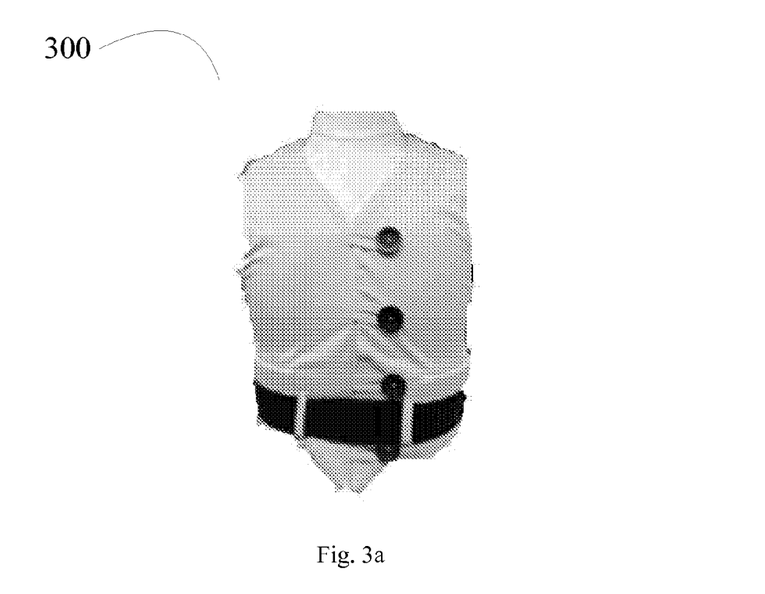
FIG. 3a and FIG. 3b, is an exemplary diagram of a preferred embodiment of the disclosed device.

In another preferred embodiment the device for determining if predetermined conditions for the first physiological parameter measurement of a subject are met is disposed in a garment 300, as shown in FIG. 3a, suitable for being worn by a subject in a predefined way. Garments which house electronic devices including sensors are known in the art. They are known in the art as wearable electronics, functional electronic garments or clothing. They may be made out of textiles referred to as E-textiles or electronic textiles or smart textiles. It is possible to embed electronic devices in an article of clothing or garment and the functional interconnections are also provided by the textile. No further details of these are described here except what is applicable to this disclosure since a person familiar with the field will readily understand what is meant here.

Figure 3B:
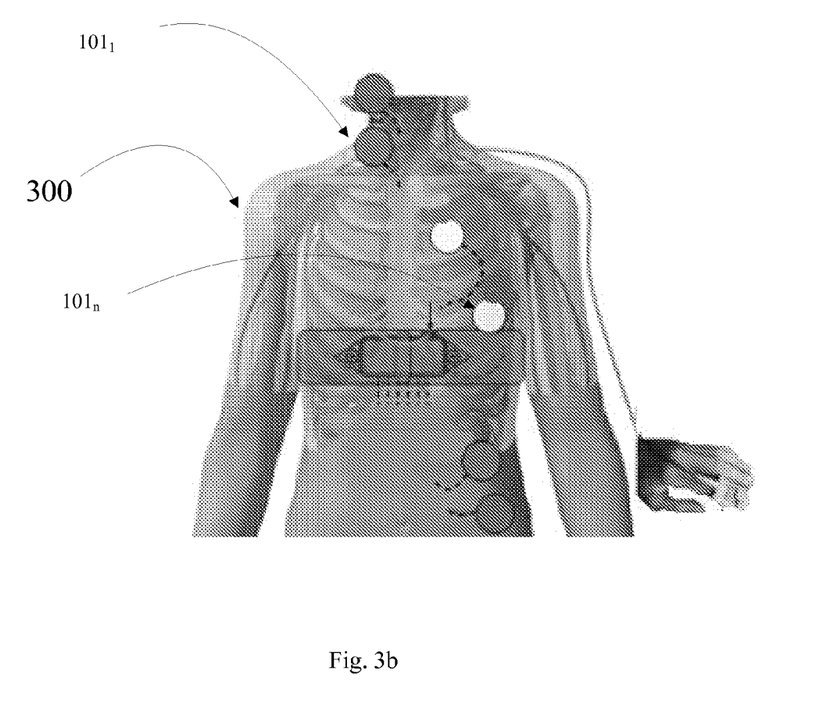

When the disclosed device is disposed in such a garment, say something similar to a waistcoat, a coat or a coverall, made out of such textiles, the sensors $101_1, 101_2, \ldots 101_n$, for sensing the second and/or first physiological parameters are located in the garment so that when the garment is worn as intended, the sensors are in contact with the subject's body surface such that they can perform their intended function i.e., sense the physiological parameter each is intended to measure, as shown in an exemplary way in FIG. 3b. The interconnections between the sensors and the rest of the device are provided by the textile itself. The sensors may communicate with the rest of the device wirelessly as well. Thus, from the perspective of the subject, he has to wear the garment as predefined, assume the recommended physical position and start the device for the function of the device to be carried out automatically. This embodiment may provide the advantage that the subject does not need any assistance, for example that of a caregiver, to apply the sensors to the right places on his own body. This may also make the measurement of the first physiological parameter (for example the BP) by the subject himself at home without visiting a care facility repeatable and dependable. With the appropriate communication means incorporated into the device, the first physiological parameter measurement and the context data may be sent to a remote location—for example a hospital, for the experts or a remote system or application to monitor the subject.

Figure 4:
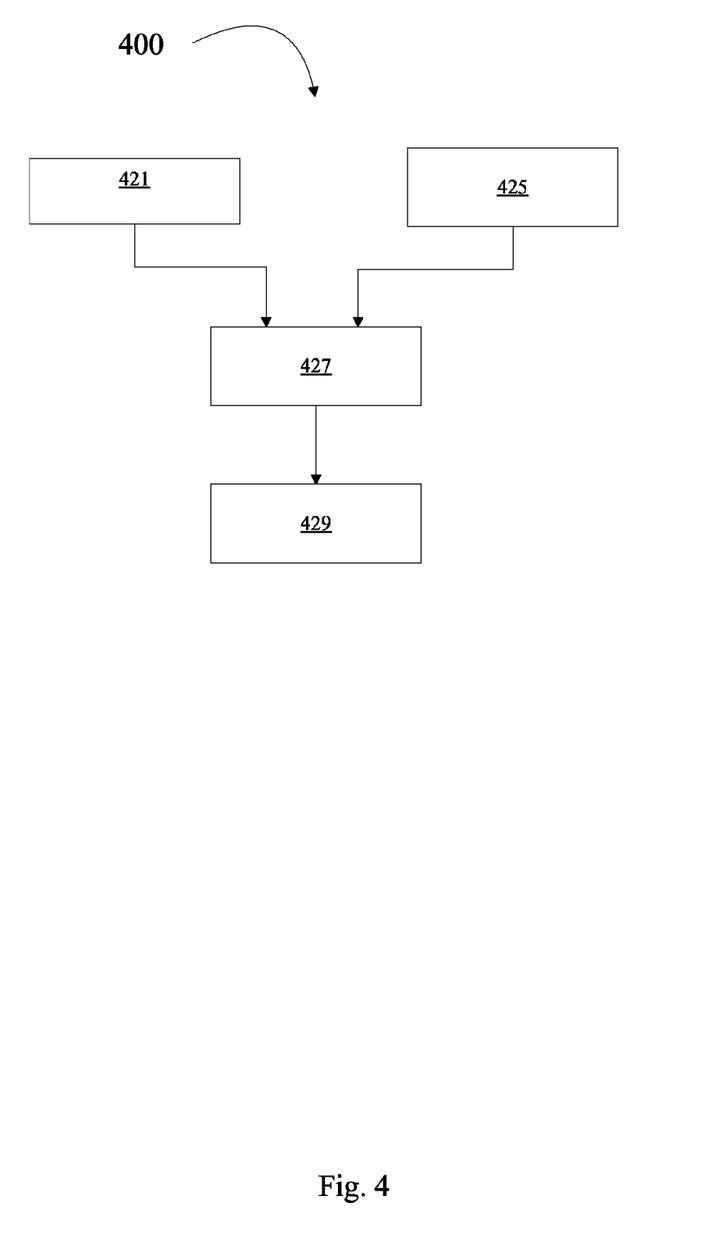
FIG. 4 is a diagrammatic representation of the disclosed method.

The method of determining if predetermined conditions for a first physiological parameter measurement of a subject are met is shown as a flow diagram in FIG. 4. In a first measuring step 421, at least one second physiological parameter is measured. In a second measuring step 425 at least one environmental parameter is measured. In a determining step 427 it is determined if the predetermined conditions are met, based on the values of the measured second physiological parameters and environmental parameters, to determine whether a first physiological parameter measurement may be made at a present time or not. In an outputting step 429, the decision that the predetermined conditions for a first physiological parameter measurement of the subject are met is outputted for further use.

In one embodiment of the method, the output is in a human readable form. In that case a caregiver may read it and measure the first physiological parameter once the decision output is that first physiological parameter may be measured.

Figure 5:
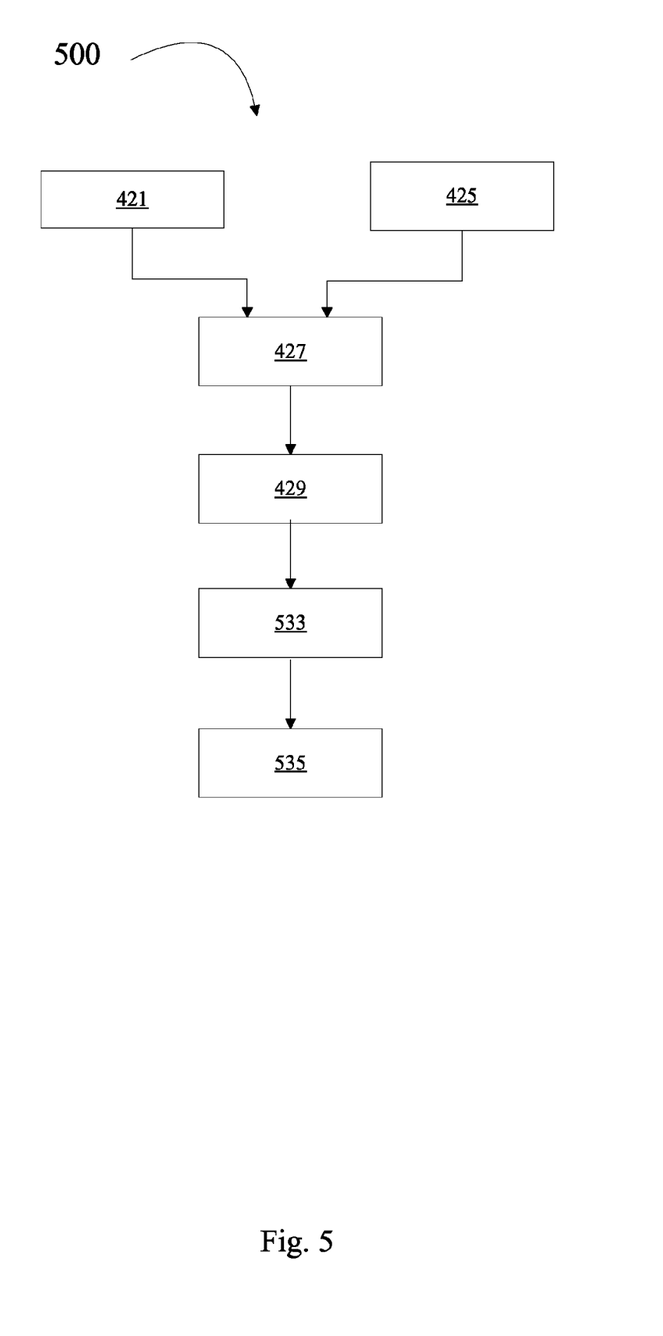
FIG. 5 is a diagrammatic representation of a variant of the disclosed method.

In another embodiment of the method 500, shown in FIG. 5, in a first physiological parameter measurement step 533, the first physiological parameter measurement is made. Then the first physiological parameter value and all the values of the second physiological parameters and environmental parameters at the time of measurement are outputted in an outputting step 535.

The first physiological parameter measurement is enabled as long as the predetermined conditions for the measurement of the first physiological parameter are met. That means, the context continues to be evaluated during the measurement of the first physiological parameter and if the predetermined conditions are not met, it will be indicated and the measurement of the first physiological parameter is stopped by the caregiver or the first physiological parameter measurement are disabled. There can be more than one possible reason for the context to change. For instance the subject may speak during the measurement. This is known to introduce artifacts in a BP measurement, for instance. The subject may move his arm or change his body position which will also make the measurement of the first physiological parameter undependable. There may be a sudden disturbing external audible noise that disturbs the subject and so on. When such conditions inimical to the measurement are encountered, the measurement is disabled automatically and enabled again when the measurement may be made again based on the context.

The gist of the method of determining if predetermined conditions for a physiological parameter measurement of a subject are met is to measure multiple physiological and environmental parameters that may not only be overlapping but may also appear to be redundant. The apparently redundant measurements are used to determine and cross check if the measurement may be made. The redundancy is used for cross-checking the values of the parameters measured in different ways to increase the dependability of the measurement.

For example, it is possible to practice the invention in an arrangement wherein there are more than one memory unit to store the various signals. While the physiological and environmental sensor signals are being acquired for measuring the physiological and environmental parameters, they may be digitized and stored in a temporary volatile memory and after the processing and comparison the values may be stored in a non-volatile memory. Even though the physiological and environmental parameters are treated as distinct, processing means and memory means to determine the physiological and environmental parameters may carry out the functions for the physiological as well as the environmental parameter measurements. Similarly, the steps of methods disclosed in different embodiments may be combined with advantage. Further variations and combinations will occur to a practitioner and all such variations are deemed to be within the scope of the disclosed devices and methods. Others may add more parameters or use lesser number of parameters than those recited to determine that predetermined conditions are met and all such variations are deemed to be within the scope of the disclosed embodiments and methods.

Self measurements of physiological parameters such as blood pressure are prone to errors and artifacts since they are often not done according to established and standardized protocols i.e., such that predetermined conditions for a reliable measurement are not met. The device and method as defined in the claims are used to determine whether the predetermined conditions for a reliable measurement are met. With one or more physiological and environmental sensors a measurement context is determined. The context for dependable measurements is for example known from protocols. The obtained sensor data is compared with predetermined thresholds to determine whether the context allows a reliable self test. In case the predetermined conditions are not met based on the obtained sensor data instructions are given to guide the subject that wants to do a self test.

Other variations to the disclosed embodiments can be understood and effected by those skilled in the art, in practicing the claimed invention, from a study of the drawings, the disclosure, and the appended claims. In the claims, the word "comprising" does not exclude elements or steps other than those mentioned, and the indefinite article "a" or "an" does not exclude a plurality. A single processor or other unit may fulfill the functions of several items recited in the claims. Various means may be used for the realization of the processing of the signals and the logic units, such as general purpose microprocessors, microcontrollers, programmable logic devices and such or dedicated hardware or combination of hardware and software may also be used. The mere fact that certain measures are recited in mutually different dependent claims does not imply that a combination of these measures cannot be used to advantage.

The invention claimed is:
1. A device for determining if predetermined conditions for measuring a first physiological parameter of a subject are met, the device comprising:
  one or more physiological sensors for measuring one or more second physiological parameters of the subject;

one or more environmental sensors for measuring one or more environmental parameters from the environment of the subject;
a decision unit for:
determining if the predetermined conditions are met based on the values of the one or more second physiological parameters and the values of the one or more environmental parameters; and
if the predetermined conditions for measuring the first physiological parameter are not met, discarding automatically acquired measurements of the first physiological parameter; and
an output unit for outputting that the predetermined conditions for measuring the first physiological parameter of the subject are met, wherein the output unit is further arranged to give instructions to guide the subject in case the predetermined conditions are not met.

2. The device of claim 1, wherein the one or more physiological sensors for measuring the one or more physiological parameters include one or more of ECG electrodes, skin temperature sensors, skin electrical resistance sensors, heart sound sensors, thoracic impedance sensors, infrared Photoplethysmography sensors, near-infrared Photoplethysmography sensors, Respiratory Inductance Plethysmography sensors, three-axis accelerometers, microphones and cuff-based sphygmomanometer sensors.

3. The device of claim 1 wherein the one or more environmental sensors includes accelerometer sensors.

4. The device of claim 1 wherein the first physiological parameter is a blood pressure.

5. The device of claim 4 further comprising a blood pressure sensor for measuring the blood pressure, and the device being arranged to acquire the blood pressure values from the blood pressure sensor during a period in which the output unit outputs that the predetermined conditions for a blood pressure measurement of the subject are met; and
wherein the output unit is further arranged for outputting the blood pressure values for further use.

6. The device of claim 1, wherein the one or more environmental sensors further include a microphone.

7. The device of claim 1, wherein the one or more environmental sensors comprise:
a first microphone configured to sense an environmental noise; and
a second microphone configured to measure a voice of the subject.

8. The device of claim 1, wherein the predetermined conditions are based on at least one of:
a sex of the subject;
an age of the subject;
a level of fitness of the subject; and
a medical history of the subject.

9. The device of claim 1, wherein the predetermined conditions are based on:
a sex of the subject;
an age of the subject;
a level of fitness of the subject; and
a medical history of the subject.

10. The device of claim 1, wherein the one or more environmental sensors include:
an air temperature sensor;
a microphone; and
a humidity sensor.

11. The device of claim 1 wherein the one or more environmental sensors includes an atmospheric pressure sensor.

12. The device of claim 1 wherein more than one type of physiological sensors are used for measuring either the first physiological parameter or the second physiological parameter.

13. The device of claim 1, wherein the more than one physiological sensors for measuring the one or more physiological parameters include all of ECG electrodes, skin temperature sensors, skin electrical resistance sensors, heart sound sensors, thoracic impedance sensors, infrared Photoplethysmography sensors, near-infrared Photoplethysmography sensors, Respiratory Inductance Plethysmography sensors, three-axis accelerometers, microphones and cuff-based sphygmomanometer sensors.

14. A device for measuring a subject's blood pressure, comprising:
one or more physiological sensors for measuring the one or more physiological parameters including one or more of ECG electrodes, skin temperature sensors, skin electrical resistance sensors, heart sound sensors, thoracic impedance sensors, infrared Photoplethysmography sensors, near-infrared Photoplethysmography sensors, Respiratory Inductance Plethysmography sensors, three-axis accelerometers, microphones and cuff-based sphygmomanometer sensors;
an accelerometer configured to measure a posture of the subject;
a blood pressure sensor configured to measure the subject's blood pressure;
one or more processors configured to:
determine if predetermined conditions for measuring the subject's blood pressure are met based on the values of the one or more physiological parameters and the posture of the subject;
if the predetermined conditions for measuring the subject's blood pressure are met, control the blood pressure sensor to measure the subject's blood pressure; and
if the predetermined conditions for measuring the subject's blood pressure are not met:
determine which one or more of the physiological parameters and/or posture of the subject need to change for the decision unit to determine that the predetermined conditions are met; and
output one or more predetermined instructions in response to the determination that one or more of the physiological parameters and/or posture of the subject need to change, the predetermined instructions instructing the subject to take an action for effecting the determined changes.

15. A garment for being worn by the subject, the garment comprising the device of claim 1, the device being integrated in the garment such that in use the sensors are applied to predetermined locations on the subject's body for sensing the physiological signal corresponding to each of said predetermined locations.

16. The garment of claim 15 wherein the one or more environmental sensors are disposed on the garment for sensing the environmental parameter corresponding to each sensor.

17. A method of determining if predetermined conditions for measuring a first physiological parameter of a subject are met, the method comprising the steps of:
measuring a second physiological parameter with more than one type of physiological sensor;
measuring an atmospheric pressure with an atmospheric pressure sensor;

determining that the predetermined conditions for measuring the first physiological parameter are not met based on the values of the one or more second physiological parameters and the atmospheric pressure; and in response to the determination that the predetermined conditions are not met:
(i) providing instructions to guide the subject; and
(ii) discarding automatically acquired measurements of the first physiological parameter.

18. The method of claim 17 wherein the first physiological parameter is a blood pressure.

19. The method of claim 17 wherein:
the determining further includes determining a second physiological parameter of the one or more second physiological parameters whose value needs to change to meet the predetermined conditions; and
the outputting further includes outputting predetermined instructions to the subject, based on the first physiological parameter and the values of one or more of the second physiological parameters, for taking actions for effecting a change in the value of the second physiological parameter whose value need to change, such that the predetermined conditions are met.

20. A system for determining if predetermined conditions for measuring a first physiological parameter of a subject are met, the system comprising:
one or more physiological sensors for measuring one or more second physiological parameters of the subject;
an atmospheric pressure sensor for measuring an atmospheric pressure;
one or more processors configured to:
determine if the predetermined conditions for measuring the first physiological parameter are met based on the values of the one or more second physiological parameters and the value of the atmospheric pressure;
output that the predetermined conditions for measuring the first physiological parameter of the subject are met; and
if the predetermined conditions are not met:
(i) give instructions to guide the subject; and
(ii) discard automatically acquired measurements of the first physiological parameter.

* * * * *